(12) United States Patent
Reddy et al.

(10) Patent No.: US 6,465,692 B1
(45) Date of Patent: Oct. 15, 2002

(54) REAGENTS FOR PREPARING A SAMPLE CONTAINING BIOMOLECULAR ANALYTES FOR CAPILLARY ELECTROPHORETIC SEPARATION AND METHODS FOR MAKING THE REAGENTS

(75) Inventors: M. Parameswara Reddy, Brea, CA (US); Chitra K. Ratnayake, Yorba Linda, CA (US); Yu Liu, Rowland Heights, CA (US); Jirong Gu, Irvine, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 09/469,675

(22) Filed: Dec. 22, 1999

(51) Int. Cl.$^7$ ............... C07C 233/03; C07C 231/22
(52) U.S. Cl. ............... 564/215; 564/216; 514/629; 204/451
(58) Field of Search ............... 564/215, 216; 514/629; 204/451

(56) References Cited

U.S. PATENT DOCUMENTS 4,687,732 A * 8/1987 Ward et al. ............ 435/6
5,891,313 A * 4/1999 Johnson et al. ............ 204/451
5,916,426 A * 6/1999 Madabhushi et al. ....... 204/451

OTHER PUBLICATIONS

Merck index; 4151, Eleventh edition, 1989.*
Sigma chemical, Product No. F9037, Cas No. 75–12–7, 1996.*

* cited by examiner

Primary Examiner—Shailendra Kumar
(74) Attorney, Agent, or Firm—William H. May; D. David Hill; Hogan & Hartson, LLP

(57) ABSTRACT

Formamide with low conductivity and a neutral or slightly basic pH is provided. Such formamide may be used in a sample loading solution for capillary electrophoretic separation of biomolecular analytes to enhance the efficiency of sample injection into the capillary and the intensity of the signal. Formamide of the present invention may be obtained by first purifying the formamide to a conductivity of below 7 micro mho, and then adjusting the pH of the purified formamide with a base to a range of about pH 6.5 to 7.5. The purification may be carried out by first removing the water from the formamide, and then distilling the dried formamide until the conductivity of formamide is below about 7 micro mho.

36 Claims, 2 Drawing Sheets

REAGENTS FOR PREPARING A SAMPLE CONTAINING BIOMOLECULAR ANALYTES FOR CAPILLARY ELECTROPHORETIC SEPARATION AND METHODS FOR MAKING THE REAGENTS

BACKGROUND OF THE INVENTION

1. Area of the Art

The invention relates generally to electrophoretic separation of biomolecular analytes and, specifically, to reagents for preparing biomolecular analytes for such a separation, and methods for making the reagents.

2. Description of the Prior Art

Capillary electrophoresis (CE) is a technique that has been used to separate proteins or nucleic acids, such as DNAs, from each other. See, for example, Chen, Fu-Tai A. et al., "Capillary Electrophoresis—A New Clinical Tool," Clin. Chem. 77/1:14–19 (1991); see, also, U.S. Pat. Nos. 5,120,413 and 5,228,960; see, further, U.S. Pat. No. 5,891,313. These documents are incorporated herein by reference.

In general, CE involves introduction of a sample into a capillary tube, i.e., a tube having an internal diameter of about 2 to about 2000 microns, and the application of an electric field across the tube. Eletrokinetic loading of a DNA sequencing sample mixture into a capillary electrophoresis tube is a preferred method of introducing a sample of analytes into the capillary electrophoresis tube. After the injection of the sample into the tube, an electric field is applied to the tube for separation. The electric potential of the field both pulls the sample through the tube and separates it into its constituent parts. Each of the sample constituents has its own individual electrophoretic mobility; those having greater mobility travel through the capillary tube faster than those with slower mobility. As a result, the constituents of the sample are resolved into discrete zones in the capillary tube during their migration through the tube. An on-line detector can be used to continuously monitor the separation and provide data as to the various constituents based upon the discrete zones.

The results of CE analysis are typically presented as "electropherograms", i.e., peaks of various widths and heights which correspond to the constituent parts of the sample. For example, a constituent which is present in a sample in a high concentration may evidence a peak having a large height and wide width, compared to a constituent present in a (relatively) low concentration. Typically, the electropherogram is derived by plotting detection units (typically, ultraviolet light absorbance) on the vertical axis and time of constituent traversal through the column to a detection region on the horizontal axis. Results can also be derived in terms of a unit value, typically derived from the areas bounded by the individual peaks.

In capillary electrophoretic separation, formamide is widely used to denature DNA analytes. Typically, analytes are reconstituted in formamide and heated at 90° C. for 2–3 min. to achieve denaturation prior to injection. Efficient sample injection and high-signal intensity are critical for accurate analysis. These two parameters are mainly governed by the pH and conductivity of a sample-formamide mixture.

The pH of DNA sample-formamide mixture plays an important role for DNA separation. Neutral and slightly basic pH is optimum because fluorescent dyes, such as cyanine dyes, are more stable at neutral pH. Furthermore, DNA is negatively charged above pH 6. When the sample/formamide mixture is slightly acidic, DNA is not completely ionized. This low-charge density results in inefficient sample injection and, therefore, insufficient signal intensity.

The conductivity of the DNA-formamide mixture also plays an important role for DNA separation. When the ionic strength of a DNA-formamide mixture is high due to the presence of salts, these highly mobile, smaller, negatively charged ions compete with less mobile, larger DNA fragments under applied voltage during sample injection. Therefore, small amounts of DNA fragments get injected into the capillary. As a result, a low signal will be observed, causing a low accuracy in analysis.

The most common approach to address the issue of high ionic strength is to deionize commercially available formamide by stirring it with a mixed bed resin prior to use. Commercially available formamide contains formate ions ($HCOO^-$) and ammonium ions ($NH4^+$) as the main impurities. These are the products of hydrolysis of formamide in the presence of water. These ions contribute to the high ionic strength and varying pH of formamide. By mixing with a resin carrying both $H^+$ and $OH^-$ charges, most of the ions in formamide can be removed until the capacity of the resin is exhausted.

The deionization process can be described as given in equation (1):

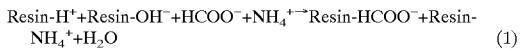
$$\text{Resin-H}^+ + \text{Resin-OH}^- + \text{HCOO}^- + \text{NH}_4^+ \rightarrow \text{Resin-HCOO}^- + \text{Resin-NH}_4^+ + \text{H}_2\text{O} \tag{1}$$

However, the deionization process does not produce formamide with consistently low conductivity and accurate pH. Therefore, a need exists to develop a new and reliable method to prepare formamide with low conductivity and optimum pH for genetic analysis applications.

SUMMARY OF THE INVENTION

It is an object of the present invention to provide formamide that may be used for preparing samples containing biomolecular analytes for electrophoretic separation with improved efficient sample injection and high-signal intensity. It is also an object of the present invention to provide methods for making such formamide.

These and other objects and advantages are achieved by the reagents and methods of the present invention. One aspect of the present invention provides formamide having a conductivity in the range of about 5 to 7 $\mu$mho and a pH in the range of about 6.5 to 7.5. Another aspect of the present invention provides a method of preparing formamide to be used for preparing samples containing biomolecular analytes for electrophoretic separation. The method comprises (a) purifying the formamide until the conductivity of the formamide is below about 7 $\mu$mho, and (b) adjusting the pH of the purified formamide from step (a) to a range of about 6.5 to 7.5. In one embodiment of the present invention, the formamide is purified by removing water contained in the formamide and distilling the dry formamide until the conductivity of the formamide is below about 7. The pH of the purified formamide may be adjusted by a base that is non-nucleophilic. A reagent comprising the formamide of the present invention is also provided.

The reagents and methods of the present invention provide a number of advantages. The formamide of the present invention, when used in a sample loading solution for preparing samples for electrophoretic separation, improves the sample loading and hence enhances the signal intensity of the separation. Particularly, compared to the regular deionized formamide, the formamide of the present invention provides significantly better performance in DNA applications. In addition, the method for preparing formamide of the present invention is reliable and reproducible.

The reagents and methods of the present invention are well-suited for use in any capillary electrophoretic separation, particularly for DNA-related applications like sequencing and fragment analysis. For example, the formamide of the present invention is well-suited for use in a sample loading solution for reconstituted nucleic acid fragments contained in a sample for capillary electrophoretic separation. Particularly, the formamide of the present invention may be used to prepare sample loading solutions as described in the co-pending U.S. patent application Ser. No. 09/447,386, filed Nov. 23, 1999, the content of which is incorporated herein by reference.

The reagents and methods of the present invention may be used in connection with a capillary electrophoresis system such as, but not limited to, CEQ™ 2000 DNA Analysis System, P/ACE™ MDQ Capillary Electrophoresis System and Paragon CZE® 2000 Capillary Electrophoresis System, which are commercially available from Beckman Coulter, Inc., Fullerton, Calif., USA.

The invention is defined in its fullest scope in the appended claims and is described below in its preferred embodiments.

DESCRIPTION OF THE FIGURES

The above-mentioned and other features of this invention and the manner of obtaining them will become more apparent, and will be best understood, by reference to the following description, taken in conjunction with the accompanying drawings. These drawings depict only a typical embodiment of the invention and do not therefore limit its scope. They serve to add specificity and detail, in which.

DETAILED DESCRIPTION OF THE INVENTION

Figure 1:
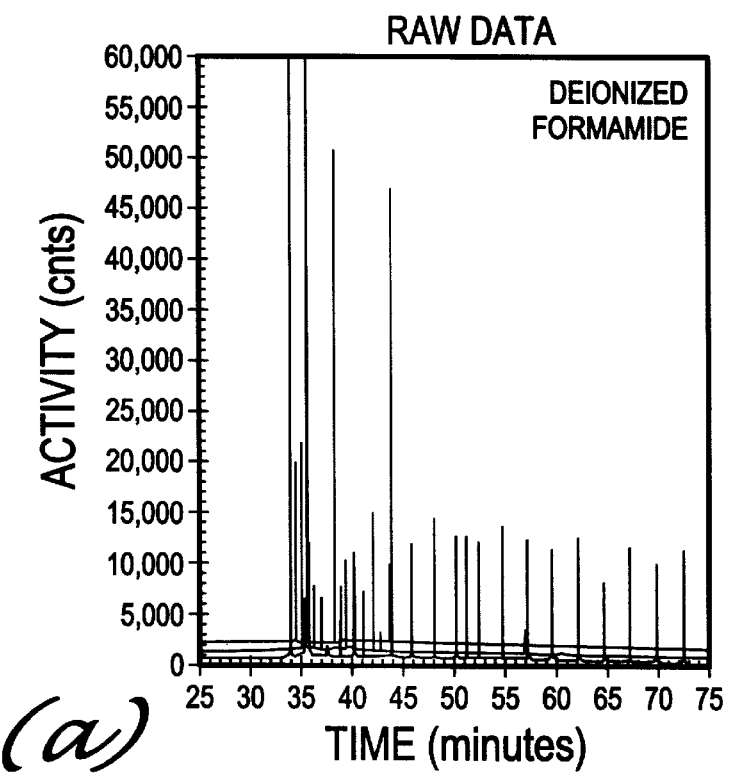
FIGS. 1(a) and 1(b) are electropherograms showing the capillary electrophoretic separation of DNA size standards by using either deionized formamide as in FIG. 1(a) or formamide of the present invention as in FIG. 1(b).
Figure 1:
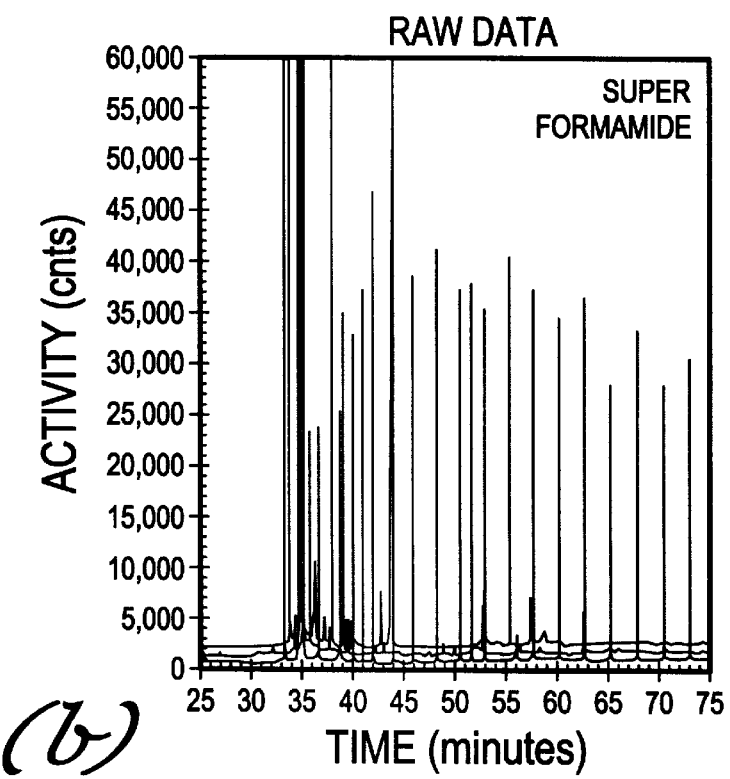

One aspect of the present invention provides formamide with low conductivity and neutral or slightly basic pH for use in genetic analysis applications. When used in a sample loading reagent for samples containing biomolecular analytes, formamide of the present invention allows efficient sample injection and high-signal intensity during electrophoretic separation of the analytes. In one embodiment of the present invention, formamide of the present invention has a conductivity in the range of about 5 to 7 μmho and a pH in the range of about 6.5 to 7.5. Formamide of the present invention is substantially moisture free. For the purpose of the present invention, formamide is substantially moisture free and hence does not undergo hydrolysis at ambient or elevated temperatures, such as 100° C. to 150° C.

Another aspect of the present invention provides methods of preparing formamide for use in electrophoretic separation of biomolecular analytes contained in a sample. In accordance with one embodiment of the present invention, the method comprises the steps of:

(a) purifying the formamide until the conductivity of the formamide is below about 7 micro mho;

(b) adjusting the pH of the purified formamide from step (a) to a range of about 6.5 to 7.5.

In one embodiment, the purification step is carried out by first removing water contained in formamide to generate a formamide that is substantially moisture free. For example, formamide, commercially available from J. T. Baker, Phillipsburg, N.J., may be mixed with dried molecular sieves for about 12–16 hrs. to generate moisture-free formamide. Clearly, any other means for removing water from formamide is also contemplated by the present invention. By removing water from formamide, hydrolysis of formamide is substantially reduced and avoided. As a result, one is able to minimize the generation of the products of formamide hydrolysis which contribute to the high ionic strength and varying pH of formamide.

The moisture-free formamide may be further purified to achieve a low conductivity. For the purpose of the present invention, the conductivity of formamide is used herein as a measure to determine the purity of formamide. The lower the conductivity, the purer the formamide. Preferably, the conductivity of formamide of the present invention is below about 7 micro mho. For example, moisture-free formamide may be further purified by distilling under a reduced pressure. After about two distillation cycles, formamide with conductivity as low as 4 micro mho may be obtained. Obviously, formamide with the desired conductivity may also be obtained by any other means known to one skilled in the art.

As discussed above, it is important for formamide of the present invention to have a neutral or a slightly basic pH. Oftentimes, double-distilled formamide is slightly acidic, and therefore a base is usually used to adjust the pH of double-distilled formamide. Preferably, a base that may be used should have the following properties:

(1) the base should be a strong base, therefore a minimal quantity is adequate to adjust the pH;

(2) the base should be non nucleophilic, therefore the base does not hydrolyze formamide or react with the biomolecules or any other molecules present in the analyte mixture; and (3) protonated base should impart the least or no conductivity to the final formamide.

For example, organic tertiary amines may be used as a base to adjust the pH of double-distilled formamide. Examples of tertiary amines include, but are not limited to, tri-ethyl amine (TEA), diisopropylethyl amine (DIPEA), and tributyl amine (TBA). In one embodiment of the present invention, TBA is used as a base to adjust the pH of distilled formamide.

Formamide of the present invention may be used in connection with electrophoretic separation of biomolecular analytes. For example, formamide of the present invention may be used to prepare a sample loading buffer for capillary electrophoretic separation of biomolecular analytes contained in a sample. In one embodiment, formamide of the present invention may be used as a solvent to prepare sample loading solutions as described in the copending U.S. patent application Ser. No. 09/447,386, the content of which is incorporated herein by reference. Briefly, a sample loading solution may comprise formamide of the present invention and a branched polymer as described in the co-pending U.S. patent application Ser. No. 09/447,386. The use of formamide of the present invention in the sample loading solution can increase the efficiency of the sample injection and the signal intensity of capillary electrophoretic separation of biomolecular analytes, such as DNA fragments, etc. The use of a branched polymer can suppress the injection of macromolecules such as DNA templates contained in the sample and, therefore, increase the efficiency of sample injection and signal intensity as well.

For the purpose of the present invention, a branched polymer may be any branched polymer defined as "that are those in which there are side branches of linked monomer molecules protruding from various center branch points along the main polymer chain." Examples of branched polymers of the present invention include, but are not limited to, branched polyvinylpyrrolidone, and the homopolymer or copolymers of vinyl pyrrolidone, acrylamide and its derivatives, ethylene glycol, ethylene oxide, vinyl alcohol, celluloses and its derivatives, dextrans and its derivatives, and mixtures of the above polymers. In accordance with one embodiment of the present invention, a branched polymer is branched polyvinylpyrrolidone. Preferably, the molecular weight of the branched polymer is in a range of about 1,200,000 to 2,000,000 dalton.

Formamide of the present invention, and sample loading solutions made with formamide of the present invention, may be used in electrophoretic separation for any biomolecular analytes. For the purpose of the present invention, the biomolecular analytes may be DNA or RNA fragments, but typically are DNA fragments, particularly DNA sequencing fragments, having a length of about 20 to 2,000 base pairs and a molecular weight range of about 6,000 to 600,000 daltons. A sample containing the biomolecular analytes may be in a solid form or a liquid form, such as a liquid nucleic acid sequencing sample mixture.

The reagents and methods of the present invention may be used in connection with a capillary electrophoresis system such as, but not limited to, CEQ™ 2000 DNA Analysis System, P/ACE™ MDQ Capillary Electrophoresis System and Paragon CZE® 2000 Capillary Electrophoresis System, which are commercially available from Beckman Coulter, Inc., Fullerton, Calif., USA.

The methods of the present invention for preparing formamide with low conductivity and neutral or slightly basic pH are reliable and reproducible. Formamide of the present invention and the sample loading reagents made with formamide of the present invention improve the sample loading efficiency and hence enhance the signal intensity. Compared to the regular deionized formamide, the super formamide gave significantly better performance in DNA applications.

The following examples illustrate various preparations and methods employed in practicing the present invention. The examples are meant to illustrate, but not to limit, the scope of the invention. Indeed, those of ordinary skill in the art can readily envision and produce further embodiments, based on the teachings herein, without undue experimentation.

EXAMPLE I

Determination of Different Amines that may be Used as a Base for Adjusting the pH of Formamide of the Present Invention Different amines were added to double-distilled formamide with conductivity 9 micro mho and pH 5–6. The results of conductivity in $\mu$ mho and pH of formamide after the addition are summarized in Table 1. The amount of base added is per 40 $\mu$L of distilled formamide. The abbreviation is indicated as following: TEA: triethyl amine; DIPEA: diisopropylethyl amine; TBA: tributyl amine.

TABLE 1

| Base | 0.2 ul | | 0.1 ul | | 0.03 ul | | 0.006 ul | | 0.003 ul | | 0.0015 ul | |
|---|---|---|---|---|---|---|---|---|---|---|---|---|
| | Cond | pH | Cond | pH | Cond | pH | Cond | pH | Cond | pH | Cond | pH |
| TEA | 50 | 10 | 44 | 10 | 32 | 8–9 | 18 | 8 | 14 | 7–8 | 12 | 7 |
| DIPEA | 45 | 10 | 42 | 10 | 34 | 8–9 | 18 | 7–8 | 12 | 7 | 11 | 6–7 |
| TBA | 17 | 8–9 | 15 | 8 | 15 | 8 | 11 | 7 | 10 | 6–7 | 9 | 6–7 |

The data shows that the addition of TBA caused the least increase of conductivity during pH adjustment. By adding 0.0015–0.006 $\mu$L TBA, the pH of double-distilled formamide can be adjusted to neutral with only a slight increase of conductivity.

EXAMPLE II

Method of Making Formamide of the Present Invention and Comparative Data Showing the Differences in Using Formamide of the Present Invention and the Conventional Formamide for Electrophoretic Separation 1. Formamide Preparation Formamide from J. T. Baker, Phillipsburg, N.J. was dried using previously dried molecular sieves, commercially available from EM Science, Gibbstown, N.J. for 12–16 hrs. This moisture free formamide was then distilled at 110° C.–120° C. under reduced pressure (2 torr). Distillate was collected in small fractions, and pH and conductivity were measured. Fractions with conductivities less than 40 $\mu$mho were combined and re-distilled in the same manner. Conductivity and pH of collected fractions from the second distillation were measured in order to get formamide with lowest conductivity. To adjust the pH, TBA was added to the double-distilled formamide to obtain TBA concentration of 0.0075% (V/V). Conductivity is usually in the range of 5–7 $\mu$mho and pH 6.5–7.5.

This formamide, referred to as "super formamide", repeatedly gave the best performance, compared to the formamide not subjected to this process or the formamide deionized with a mixed bed resin.

FIGS. 1(a) and 1(b) show the capillary electrophoretic separation of DNA size standards. The detection signal intensity with the super formamide described herein is significantly higher, compared to the deionized formamide.

Table 2 compares the signal intensities of four dye terminators reconstituted in deionized formamide and super formamide. The dye signal increased 2 to 3 times with super formamide, due to low conductivity and right pH adjustment within 6.5 to 7.5.

TABLE 2

| Sample | pH | Conductivity μmho | % Signal | | | |
|---|---|---|---|---|---|---|
| | | | DBCy7 ddATP | DBCy5 ddGTP | Cy5 ddUTP | Cy7 ddCTP |
| Deionized Formamide | 7 | 21 | 100 | 100 | 100 | 100 |
| Super Formamide | 7 | 6 | 305 | 270 | 275 | 345 |

Figure 2:
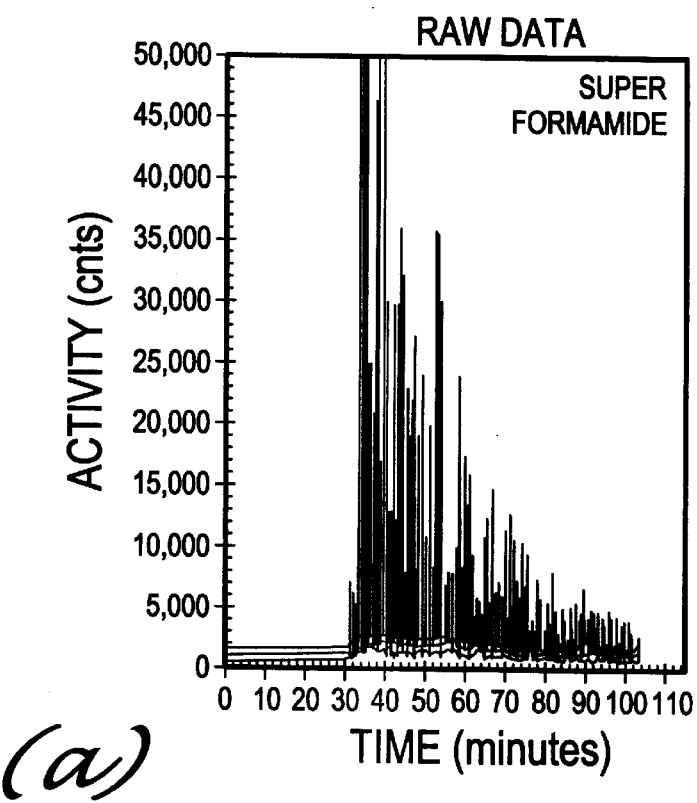
FIGS. 2(a) and 2(b) are electropherograms of sequencing fragments of C3 reconstituted in either deionized formamide as in FIG. 2(b) or the formamide of the present invention as in FIG. 2(a).
Figure 2:
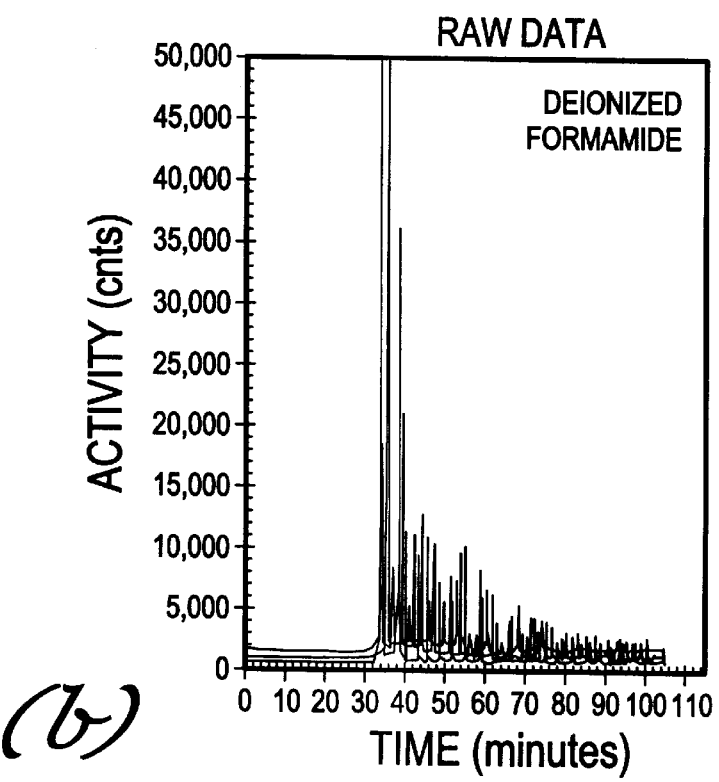

FIGS. 2(a) and 2(b) show the electropherograms of the sequencing fragments of C3 reconstituted in regular deionized formamide and super formamide. Significantly higher detection signal with super formamide is observed.

Table 3 shows the signal intensities and base calling accuracies of sequencing fragments of G2 (a plasmid containing Mouse Glucokinase insert) and C3. The detection signal of fragments made from very low template quantity (5–15 fmole) is significantly higher, compared to deionized formamide resulting in relatively high-base calling accuracy.

TABLE 3

| Formamide sample | DNA template | Signal (Counts) | % pass (98% accuracy) |
|---|---|---|---|
| Super formamide | 5 fmol C3 | 13,800 | 87.5 |
| | 15 fmol C3 | 23,800 | 87.5 |
| | 5 fmol G2 | 5,300 | 62.5 |
| | 10 fmol G2 | 10,600 | 100 |
| Deionized formamide | 5 fmol C3 | 4,300 | 0 |
| | 15 fmol C3 | 9,600 | 75 |
| | 5 fmol G2 | 2,800 | 14.3 |
| | 10 fmol G2 | 4,100 | 71.4 |

EXAMPLE III

Results of Sample Loading Solution Made with Formamide of the Present Invention

Sample loading solution as described in the co-pending U.S. patent application Ser. No. 09/447,386 made from super formamide is used to reconstitute the fragments of plasmid C3 and delta 155 to obtain a stable current and, therefore, accurate base-call. Table 4 shows the signal intensities and base calling accuracies of sequencing fragments of fragments C3 and delta 155 plasmid.

TABLE 4

| SLS | DNA template | Signal (Counts) | % pass (98% accuracy) |
|---|---|---|---|
| Super formamide-SLS | 30 fmol C3 | 14,800 | 87.5 |
| | 30 fmol delta 155 | 14,000 | 85.7 |
| Deionized formamide-SLS | 30 fmol C3 | 12,100 | 75 |
| | 30 fmol delta 155 | 12,900 | 85.7 |

Table 4 indicates that superior results were achieved by using formamide of the present invention.

The present invention may be embodied in other specific forms without departing from its essential characteristics. The described embodiment is to be considered in all respects only as illustrative and not as restrictive. The scope of the invention is, therefore, indicated by the appended claims rather than by the foregoing description. All changes which come within the meaning and range of the equivalence of the claims are to be embraced within their scope.

What is claimed is:

1. Formamide with a conductivity below 10 micro mho and a pH in the range of about 6 to 8.5.

2. The formamide of claim 1 being substantially moisture free.

3. The formamide of claim 1 being distilled.

4. A method of using the formamide in claim 1 for the analysis of biomolecular analytes.

5. The method of claim 4, wherein the biomolecular analyte is DNA.

6. A method of preparing formamide for use in electrophoretic separation of biomolecular analytes, comprising:
   (a) purifying the formamide until the conductivity of the formamide is below about 10 micro mho; and
   (b) adjusting the pH of the purified formamide from step (a) to a range of about 6 to 8.5.

7. The method of claim 6, wherein purifying step (a) further comprises the steps of:
   (a) removing the water contained in the formamide to produce a formamide that is substantially moisture free; and
   (b) distilling the substantially moisture-free formamide to generate a purified formamide with a conductivity that is less than 10 micro mho.

8. The method of claim 7, wherein in step (a) the formamide is treated with moisture-free molecular sieves for removing the water of the formamide.

9. The method of claim 7, wherein in step (b) the distilling step is repeated.

10. The method of claim 9, wherein the purified formamide has a conductivity that is about 4 micro mho.

11. The method of claim 6, wherein in step (b) the pH of the purified formamide is adjusted by a base.

12. The method of claim 11, wherein the base is a non-nucleophilic base.

13. The method of claim 11, wherein the base is an organic tertiary amine.

14. The method of claim 13, wherein the base is selected from the group consisting of triethyl amine (TEA), Diisopropylethyl amine (DIPEA), and tributyl amine (TBA).

15. The method of claim 14, wherein the base is TBA.

16. A reagent for preparing a sample containing biomolecular analytes for capillary electrophoretic separation, comprising formamide having a conductivity below 10 micro mho and a pH in the range of about 6 to 8.5.

17. The reagent of claim 16, wherein the formamide is substantially moisture free.

18. The reagent of claim 16, wherein the reagent further comprises a branched polymer.

19. A method of using the reagent in claim 18 for the analysis of biomolecular analytes.

20. The method of claim 19, wherein the biomolecular analyte is DNA.

21. The method of claim 18, wherein the branched polymer is selected from the group consisting of branched polyvinylpyrrolidone, and the like.

22. The method of claim 21, wherein the branched polymer is branched polyvinyl pyrrolidone.

23. The method of claim 22, wherein the molecular weight of the branched polyvinylpyrrolidone is in a range of about 1,200,000 to 2,000,000 daltons.

24. A method for preparing a sample containing biomolecule analytes for capillary electrophoretic separation comprising the steps of:
   (a) providing a reagent comprising formamide having a conductivity below 10 micro mho and a pH in the range of about 6 to 8.5; and (b) mixing the sample with the reagent prior to the capillary electrophoretic separation of the analytes.

25. The method of claim 24, wherein the formamide is moisture free.

26. The method of claim 24, wherein the formamide is double distilled.

27. The method of claim 24, wherein the formamide has a conductivity that is about 4 micro mho.

28. The method of claim 24, wherein the pH of the formamide is adjusted by a base.

29. The method of claim 28, wherein the base is a non-nucleophillic base.

30. The method of claim 28, wherein the base is an organic tertiary amine.

31. The method of claim 30, wherein the base is selected from the group consisting of tri-ethyl amine (TEA), Di-isoporpylethyl amine (DIPEA), and tributyl amine (TBA).

32. The method of claim 31, wherein the base is TBA.

33. The method of claim 24, wherein the reagent further comprises a branched polymer.

34. The method of claim 33, wherein the branched polymer is selected from the group consisting of branched polyvinylpyrrolidone, and the like.

35. The method of claim 34, wherein the molecular weight of the branched polyvinylpyrrolidone is in a range of about 1,2000,000 to 2,000,000 daltons.

36. The method of claim 24, wherein the biomolecule analyte is DNA or RNA.

* * * * *